(12) United States Patent
Cheikh (10) Patent No.: US 6,349,850 B1
(45) Date of Patent: Feb. 26, 2002

(54) METHOD FOR PREPARING AN INJECTABLE PREPARATION AND DEVICE FOR IMPLEMENTING SAME

(75) Inventor: Roland Cherif Cheikh, Issy les Moulineaux (FR)

(73) Assignee: Societe de Conseils de Recherches et D'Applications Scientifiques SCRAS, Paris (FR)

( * ) Notice: Subject to any disclaimer, the term of this patent is extended or adjusted under 35 U.S.C. 154(b) by 0 days.

(21) Appl. No.: 09/194,918
(22) PCT Filed: Jun. 4, 1997
(86) PCT No.: PCT/FR97/00989
§ 371 Date: Feb. 18, 1999
§ 102(e) Date: Feb. 18, 1999
(87) PCT Pub. No.: WO97/46202
PCT Pub. Date: Dec. 11, 1997

(30) Foreign Application Priority Data

Jun. 4, 1996 (FR) .............................. 96 06886

(51) Int. Cl.$^7$ .................................. A61J 1/00
(52) U.S. Cl. .......................... 222/1; 222/152; 206/222; 206/365; 141/9; 141/100; 141/25
(58) Field of Search .............................. 222/145.5, 152, 222/1; 206/219, 222, 365; 141/9, 18, 21, 25–27, 67, 329, 330, 100, 105

(56) References Cited

U.S. PATENT DOCUMENTS

| | | | |
|---|---|---|---|
| 3,810,469 A | 5/1974 | Hurschman | .................. 604/88 |
| 4,243,080 A | 1/1981 | Choksi et al. | |
| 4,346,820 A * | 8/1982 | Cavazza | ...................... 206/222 |
| 5,334,162 A | 8/1994 | Harris | |
| 5,551,778 A * | 9/1996 | Hauke et al. | ................ 206/222 |
| 5,588,745 A * | 12/1996 | Tanaka et al. | ............... 206/222 |
| 5,791,466 A * | 8/1998 | Tsals | ........................... 206/222 |

FOREIGN PATENT DOCUMENTS

| | | |
|---|---|---|
| EP | 0 161 797 | 11/1985 |
| EP | 0 499 481 | 8/1992 |
| EP | 0 520 618 | 12/1992 |
| WO | WO 94/06690 | 3/1994 |
| WO | WO 96/29113 | 9/1996 |

* cited by examiner

*Primary Examiner*—J. Casimer Jacyna
(74) *Attorney, Agent, or Firm*—Young & Thompson

(57) ABSTRACT

A method comprising the following steps: preparing in a vacuum a dry form (18) of an active principle, as well as a liquid (22), and drawing this liquid into the dry form, by the action of the vacuum to obtain an injectable preparation. The device comprises a gastight syringe (19) to condition under vacuum the dry form, a reservoir (12) containing the liquid (22) and a cap (29) forming a connector between the syringe and the liquid reservoir, the injection needle (25) of the syringe being driven into the septum (24) of the cap (29). The invention enables a preparation which is directly injectable by an automatic rehydration step to be obtained; indeed, after activation, the extemporaneous preparation is automatic since the device elements move by themselves under the action of the liquid which is drawn by suction into the volume under vacuum containing the solid formulation (18).

26 Claims, 9 Drawing Sheets

METHOD FOR PREPARING AN INJECTABLE PREPARATION AND DEVICE FOR IMPLEMENTING SAME

CROSS REFERENCE TO RELATED APPLICATION

This is the 35 USC 371 national stage of international application PCT/FR97/00989 filed on Jun. 4, 1997, which designated the United States of America.

FIELD OF THE INVENTION

The present invention provides a process for preparing an injectable pharmaceutical preparation, a device for implementing said process and the product obtained by implementing the process by means of the device.

BACKGROUND OF THE INVENTION

It is known that injectable forms are immediately bioavailable and constitute a potential passive mode of administration for the patient and an ideal treatment in urgent cases.

Another important reason for the development of parenteral forms is the use of active principles (AP) which are degraded and/or not significantly absorbed by the oral route.

Of all these AP which, for various reasons, require an injectable form, many of them are unstable in aqueous media, whether in solution, suspension or dispersion.

In order to avoid hydrolysis and all the physico-chemical problems associated with a liquid presentation (precipitation, aggregation, adsorption, crystallisation), a presentation is often used in which the AP is preserved in a solid, dried or freeze-dried form.

The preparation of the liquid form required for injection then takes place extemporaneously, just prior to injection.

This preparation consists in hydrating the solid form with the liquid medium for solubilisation or suspension of the AP.

Traditionally, this operation is carried out in a sealed bottle which contains the solid form. The liquid is introduced into the bottle by a syringe, the needle of which is capable of piercing a stopper-septum.

The liquid form is then recovered in the syringe so that it can be injected.

The time required for this delicate operation and the risks of contamination it involves led experts in medical technology to devise devices for making extemporaneous preparation simpler and more reliable, and for using the fewest possible components.

Along such lines, the patents EP-A-0 664 136, DAIKYO SEIKO, EP-0 599 649 PHARMACIA, WO-95 11051 disclose a bicompartmental or "by-pass" syringe which combines in the same syringe the liquid medium and the solid form which will be directly rehydrated in the syringe before injection.

Similarly, certain producers propose devices which combine the bottle with the syringe and control the satisfactory execution of the preparation (French patents DEBIOTECH 2 705 898, 2 715 311, 2 717 086).

Certain faults in the traditional systems are not, however, solved by said new devices, which pose problems of loss of preparation in their dead volumes, which do not render rehydration automatic and static but keep it manual and dynamic, that is, the flow of liquid and the transfers after hydration displace the solid form and, in particular, the AP.

The injectable form does not, therefore, necessarily have the same distribution or homogeneity as the dry form. This constitutes a problem, particularly in the case of suspensions.

The fact that preparation is dynamic and carried out manually may lead to important differences depending on the operator, the speed with which he acts, the manner in which he loads the liquid and controls the evacuation of the air. Finally, the force with which the solid AP is hydrated is likely to lead to a relatively substantial emulsion of microbubbles of air.

The time allowed for solubilisation or suspension and agitation of the liquid medium determines the homogeneity of the preparation.

In the case of suspensions, poor homogeneity or the onset of sedimentation may lead to dose and administration problems.

The object of the invention is to propose a process for overcoming these various disadvantages.

SUMMARY OF THE INVENTION

According to the invention, the process for preparing an injectable preparation is characterised in that a dry form of an active principle under vacuum and a liquid are prepared, and said liquid is introduced into the dry form by suction by virtue of the action of the vacuum in order to form the said injectable preparation.

The process of preparation and packing under vacuum according to the invention avoids the above-mentioned problems (dead volume, manual activation, injectability) and at the same time the problems of injected liquid formulation (homogeneity, degassing).

According to a characteristic of the process, the dry form under vacuum occupies the same volume as the final form obtained after automatic hydration by a corresponding, exactly pre-determined volume of liquid.

According to an embodiment of the process of the invention, a layer of excipient is added to the dry form, said layer being used subsequent to the injectable preparation as a liquid piston in order to push the other layers and to reduce the losses of active principle during injection.

According to another embodiment of the process of the invention, the dry form is packed in a syringe fixed to an automatic rehydration device; in order to prepare the dry form, a liquid containing the active principle is frozen, a specific quantity of excipient solution is added to the surface of the frozen liquid, this excipient solution is frozen, the whole unit is freeze-dried so as to obtain, between the piston of the syringe and the solid of active principle under vacuum, a volume of freeze-dried product containing only the excipient which, after automatic rehydration and movement of the piston in order to empty the syringe, occupies a dead volume at the bottom of the syringe and of the injection needle at the end of injection.

This process of preparation and packing leads to automatic rehydration: it is sufficient for the user to activate the device for the liquid to restore the solid form to the state it was in prior to drying or freeze-drying. Activation of the device consists in bringing into contact the liquid volume and the solid volume under vacuum. After activation, extemporaneous preparation is automatic, that is, the components of the device move solely under the action of the liquid which is drawn by suction by the vacuum under which the solid formulation is placed.

This property of vacuum packing is independent of the operator, and hydration leads to an immediate return to the situation of the liquid form prior to drying or freeze-drying.

The solid form and active principle remain static during this hydration, that is, they are not displaced by the liquid.

This immediate preparation is thus directly injectable without the need to agitate it, transfer it or expel the air before injection.

This process of preparation and packing may use certain devices or containers currently available, provided that they ensure that the form under vacuum is kept under vacuum until rehydration. The component(s) of the device must allow this rehydration whilst avoiding contact with the ambient air.

This feature also leads to certain specific devices or components for this process of preparation and packing. These devices and components will be described below.

The techniques for vacuum packing the solid form in the device and the packaging are derived from existing techniques (blood sampling tube, packing under a plastic film). This vacuum packing of the solid form and of the AP is, moreover, capable of replacing inert gas blanketing (nitrogen) and improving the stability of the preparation particularly at high temperatures (thermal insulation) and the compatibility with the container (contact insulation).

The above-mentioned advantages of the process and of the devices of the invention, which will be explained below, are particularly important for certain preparations:

For a solid, readily solubilised preparation, the advantage is that of obtaining immediately a degassed liquid preparation without air bubbles.

For a solid preparation which is more difficult to solubilise, either due to its viscosity or due to the time required for solution, the formulation under vacuum avoids the emulsion of air in the liquid, simplifies and accelerates solubilisation.

For a suspension and, more especially, for a sustained-release suspension of microspheres (Decapeptyl 3.75 B.1), the formulation under vacuum avoids the problems of dehomogenisation and the risks of precipitation, hence blocking off whilst reducing the time required for reconstitution.

The pharmaceutical preparation under vacuum and the preloaded device make it possible to reduce considerably the dead volume and hence the losses of active principle.

Finally, for a dispersion and more particularly for semi-solid forms, the very high viscosity of the hydrated form makes it practically indispensable to use a process of preparation and packing under vacuum for the dry form.

The non-liquid or semi-solid aqueous form obtained after hydration under vacuum is, moreover, likely to have salting out properties which are different to and better than those of a form hydrated in air. The fact of not having trapped air in the dispersion makes it possible to reduce the volume for the same quantity (which improves salting out) and avoids rupture of the in situ depot structure which may also modify salting out.

The process, packing and devices are described here for aqueous liquid forms. It goes without saying that the whole of the invention applies with the same advantages to liquid forms (solution, suspension or dispersion) which are reconstituted from a mixture of water-organic solvent, from an organic solvent, or from other liquids such as injectable oils.

The speed of the process of preparation and its realisation in a hermetic packing compensates for the viscosity or the risks of evaporation of certain liquids.

The device for implementing the process according to the invention is characterised in that it comprises means of vacuum packing a dry form, means of packing an extemporaneous rehydration liquid, and of connection between these means in order to add, by suction, the liquid to the dry form.

According to a preferred embodiment, the means of vacuum packing the dry form are a gastight syringe and the means of packing liquid are a reservoir containing a piston.

The syringe is preloaded with the solid form under vacuum, the packing of which allows immediate injection after hydration without agitation, and avoiding the transfer of the solution or suspension through a needle from the preparation reservoir of the liquid to the syringe.

Another advantage of the vacuum-packed devices is that it is thus possible to reduce the volumes of the reservoirs of the liquid and solid whilst increasing the precision of the volume injected.

In fact, the absence of air makes it possible to fill completely the compartment containing the solid. The volume contained in the liquid compartment may be calculated exactly in order to occupy the volume left empty in the preparation plus losses of the device. But this volume may also be in excess because it is the volume of the empty space in the solid that will determine exactly the quantity of liquid required for rehydration.

The device containing the rehydration liquid is advantageously contained in an leakproof reservoir, the volume of which may fall freely as the liquid is transferred to the reservoir of the solid form under vacuum.

This may be obtained easily, in particular, with a cartridge or with a pre-filled syringe, the piston of which moves with the movement of the liquid.

The reservoir may also be composed of a pre-filled flexible plastic bag, the flexible walls of which will follow the movement of the liquid.

The connecting element of the liquid and the vacuum shielded from the ambient air may be composed of a septum, a gate, valve or tap.

One of the characteristics of the method and of the devices is to reduce the dead volumes. This is achieved not only by reducing the volume of the connecting components (liquid-vacuum) or injection components (needle-syringe) but also by virtue of the static rehydration process which makes it possible to occupy the dead volumes with liquid without active principle, and hence without loss of injection.

Thus, the connecting component and/or the needle may be loaded with liquid without active principle in order to eliminate losses.

Moreover, it is possible, by virtue of the same static process, to provide the "liquid piston" without active principle mentioned above, which will occupy the dead volumes of the injection syringe and of the needle after administration, thus making it possible to reduce even further the losses of active principle. This is simply obtained by adding, after freezing the liquid formulation containing the active principle, a calculated volume of a solution of excipient such as mannitol, which will be frozen and freeze-dried at the same time as the formulation. By virtue of static and rapid rehydration, the two liquids, once re-formed, will hardly mix at all and the liquid without active principle will be able to push all the liquid with active principle out of the syringe and the needle (like a "liquid piston"), which will avoid losses.

In all cases (solution, suspension or dispersion), once the solid form has dried or freeze-dried, if the syringe is closed on the injection side by the connecting component, the needle or a septum, the piston is placed under vacuum with or without a blocking system, for example, inside the freeze-dryer. If the syringe is open, it can be vacuum-packed at the time of packaging under plastic film.

Even if the packing of the closed syringe is carried out beforehand under vacuum, it will be best then to pack this syringe under vacuum in such a way that the packaging, and not the syringe, ensures air-tightness during storage. This constitutes a double safety mechanism and also facilitates monitoring of the integrity of the packaging prior to use (opening).

The product or final form obtained after hydration of the solid may take one of the three forms below:

1) Solutions

The active principle combined, for example, with mannitol, is solubilised in water for injectable preparation; the solution is distributed by volume inside the syringes; the syringes are frozen and freeze-dried according to a conventional process and the solid freeze-dried product is vacuum-packed with the syringe, whether or not the syringe has been fixed beforehand to the other components of the extemporaneous rehydration device.

2) Suspensions

In the case of sustained-release microspheres, for example, the dose of microspheres is weighed into the syringe. The volume of dispersion liquid is added. The microspheres are then dispersed mechanically in the liquid. Ultrasonics are preferably used for this dispersion operation. The dispersion is then frozen rapidly, preferably in liquid nitrogen to obtain a homogeneous dispersion of the microspheres in the frozen liquid. The liquid contains the matrix of the freeze-dried product, for example, mannitol. Freeze-drying is carried out to obtain a solid in which the microspheres are suspended by the matrix in the ideal state of homogeneous dispersion of the liquid.

This solid, whether or not it is combined with the components of the automatic device for extemporaneous rehydration, is then vacuum-packed.

3) Dispersion

In the case of a semi-solid implant, for example, the semi-solid Autogel BIM 23014C, the active principle is weighed out inside a gastight metered-dose syringe.

The product obtained by implementing the process and device according to the invention comprises a dry form for parenteral administration and vacuum-packed inside an injection device also containing a liquid volume, ready to be mixed by suction with the dry form in order to reconstitute the injectable preparation.

The dry form may be a freeze-dried form or a powder obtained after removal of a solvent.

BRIEF DESCRIPTION OF THE DRAWINGS

Other features and advantages of the invention will become apparent during the description that follows, given with reference to the attached drawings which illustrate a certain number of embodiments thereof by way of non-limiting examples.

DESCRIPTION OF THE PREFERRED EMBODIMENTS

With reference to FIGS. 1 to 10, a description will first be given of an embodiment of the process for preparing an injectable preparation according to the invention, and of the rehydration device under vacuum for implementing said process.

Figure 1:
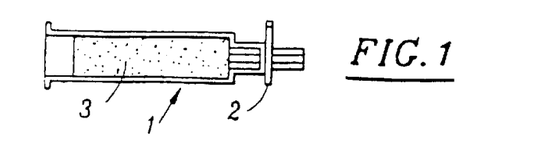
FIG. 1 is an elevation of a gastight syringe containing an active principle.
Figure 2:
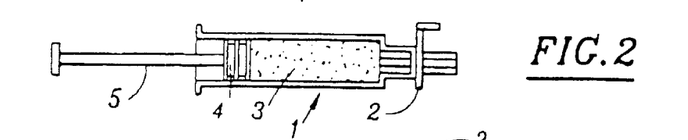
FIG. 2 illustrates the compression of the active principle in the syringe of FIG. 1.
Figures 3, 4, 5:
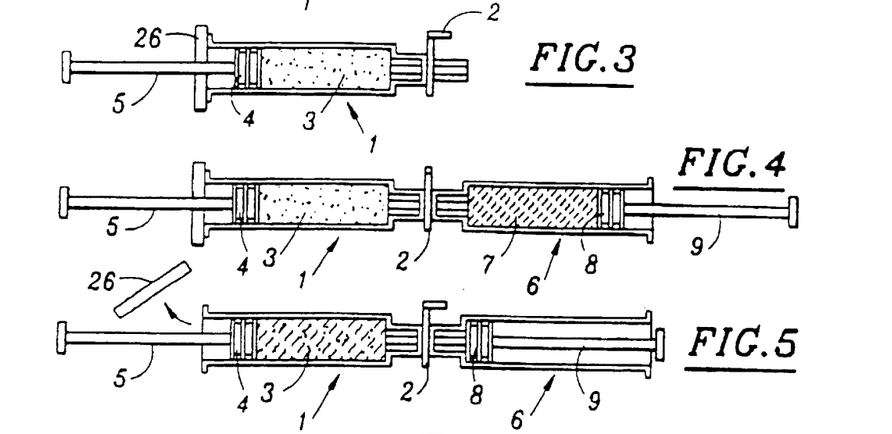
FIG. 3 illustrates the placing under vacuum of the active principle of the syringe of FIG. 2.
FIG. 4 is a longitudinal elevation of the syringe of FIG. 3 connected to a liquid reservoir by way of a valve, the latter being in the closed position.
FIG. 5 illustrates the suction of the liquid into the syringe containing the solid after the valve has been opened.

An active principle 3 is loaded into a syringe 1, fitted with a tap or valve 2 in the position of its injection needle, said active principle having been weighed and brought to a volume approximating or equal to that occupied by the semi-solid form by pressure of the piston 4 (FIG. 2) of syringe 1 before or after application of a vacuum. In FIGS. 2 and 3, it may be assumed, for example, that the active principle 3 is compressed by the piston borne by its spindle 5, prior to application of a vacuum, which operation is carried out at the stage of FIG. 3. Spindle 5 is fitted with a piece 26 for retaining the piston 4 resting on the end of syringe 1, and this because of the vacuum in the volume of the active principle 3.

Active principle 3 may be pretreated in order to adjust to the final volume and/or to promote subsequent hydration. It is thus possible to calculate its particle size distribution by grinding; spray-drying or by freeze-drying to a determined concentration.

Metered-dose syringe 1 containing the active principle under vacuum 3 is then connected (FIG. 4) by the leakproof valve 2 with the same syringe 6 containing a volume 7 of liquid for rehydration of the solid 3, for example, water. This liquid volume 7 is contained in the syringe 6 by the piston 8 and the spindle 9 of this syringe.

Then valve 2 is opened (FIG. 5) with the result that the liquid 7 passes into the solid 3 by suction under the action of the vacuum, plus, possibly, by a mechanical action on the piston 8. The retaining piece 26 may then be removed.

Figure 6:
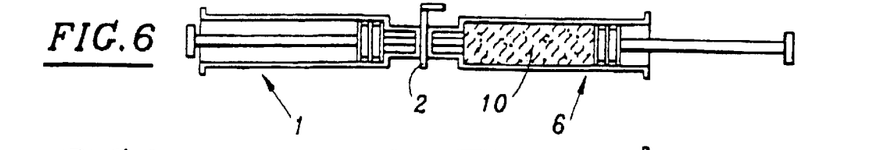
FIG. 6 represents a complementary phase of mixing between the liquid and solid by suction of said mixture into the reservoir initially filled with liquid.

The preparation is thus first mixed in syringe 1, then it is mixed again immediately or after a hydration period by the backward and forward motion from one syringe to the other (FIG. 6). This backward and forward motion is obtained by mechanical action on piston 8 and on piston 4, for example, with a syringe push or a hydraulic press.

Figure 7:
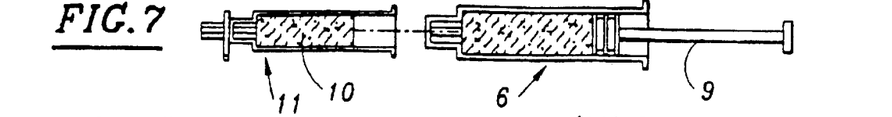
FIG. 7 illustrates a loading stage of a small syringe from the syringe previously filled and separated from the second syringe.

Once homogeneous, the mixture is distributed immediately, or after a rest period, inside small syringes such as 11 of the injection device by volumetric metering from one of the two mixing syringes 1 and 6 which are large in size. If the quantity and precision of metering into each syringe 11 does not allow direct distribution from the syringe for preparation of the mixture, particularly if the mixing syringe 6 corresponds to a large volume, an intermediate syringe of smaller diameter is used for distribution.

Syringe 11 may be, for example, one such intermediate syringe. The contents of the large syringe 6 are thus distributed in several intermediate syringes 11 of smaller capacity, each of them then being emptied in a final step into several small syringes of small capacity.

For example, from a batch prepared in 200 ml syringes 6, it is possible to use ten 10 ml syringes in order to load single 0.2 ml doses to the final syringes.

The final syringes 11 or 12 filled with semi-solid 13 and fitted with their pistons 14 and their spindles 15 (FIG. 8) are then freeze-dried and vacuum-packed, then combined (FIG. 9) with an automatic device 16 for extemporaneous rehydration. This device 16 may itself be a syringe containing the liquid 17 and connected to syringe 11 or 12 by a leakproof valve 2.

Figures 8, 9, 10:
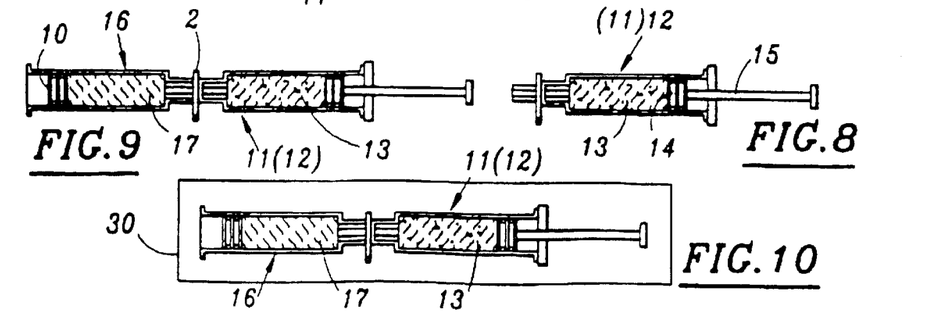
FIG. 8 is a view of the small syringe of FIG. 7 ready to be connected to a liquid reservoir.
FIG. 9 is a view of the syringe of FIG. 8 connected to a liquid reservoir with an interposed valve.
FIG. 10 is a view of the whole syringe-liquid reservoir unit of FIG. 9 packed under vacuum.

Finally, the device thus obtained (FIG. 9) is packed in a vacuum packaging 18 ready to be used for an injection of the injectable preparation which will be obtained by mixing the liquid 17 and the solid 13 by suction by virtue of the action of the vacuum under which the solid 13 is placed.

In the embodiment of FIGS. 11 to 14, the dry form 18 is packed in a syringe 19 fixed to an automatic rehydration device 21 containing a volume 22 of liquid, composed of a reservoir containing a piston 23. The freeze-dried product or solid 18 is pre-loaded under vacuum inside syringe 19 before the syringe is connected with the liquid reservoir 21.

Figure 11:
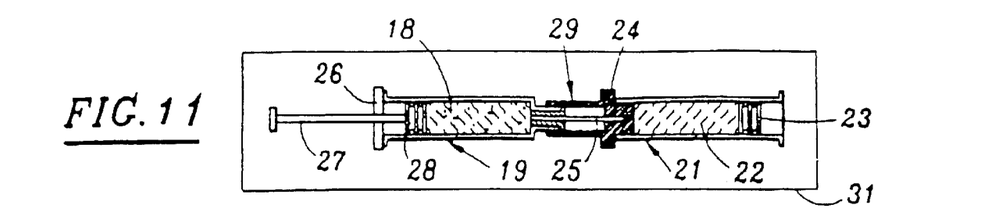
FIGS. 11 to 14 illustrate the successive stages of implementation of a first embodiment of the process and device according to the invention.

The means of connection between reservoir 21 and the syringe 19 are, in the example shown, composed of a connection 29 comprising a septum 24 in which is inserted the end of an injection needle 25 of syringe 19. The syringe is also fitted with a piece 26 keeping the spindle 27 and its piston 28 in a suitable position, in view of the vacuum under which the solid 18 is placed. The whole device is vacuum-packed in a flexible packaging 31.

Figure 12:
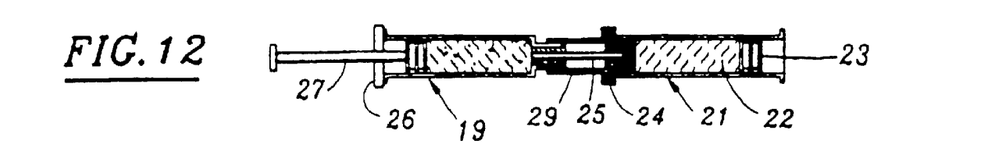
Figures 13, 14, 15:
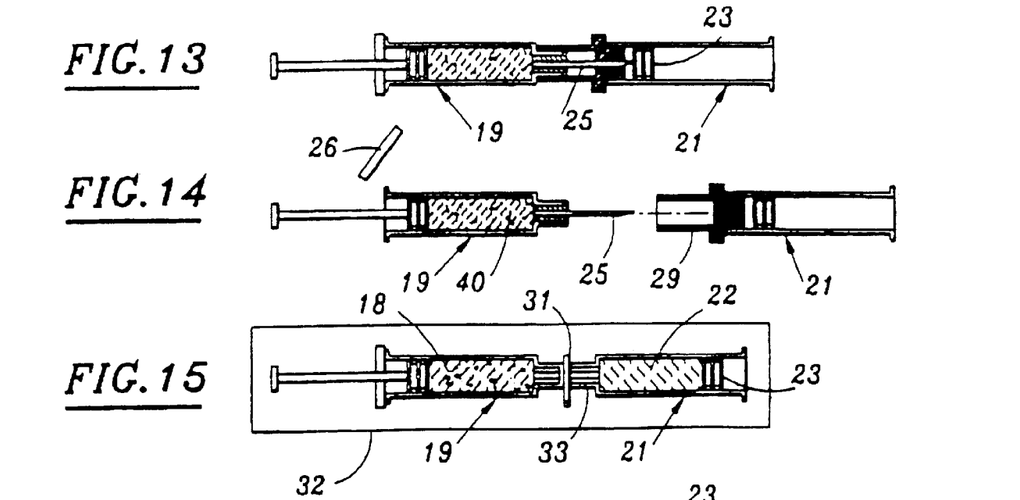
FIGS. 15 to 17 are elevations similar to FIGS. 11 to 14 illustrating the implementation of a second embodiment of the device according to the invention.

In order to obtain the injectable preparation from the device of FIG. 11, the packaging 31 is first removed, then the syringe 19 is pushed by its spindle 27 so as to insert the needle 25 in the septum 24 (FIGS. 12, 13). When the end of the needle 25 penetrates the volume of liquid 22, said liquid is sucked by the vacuum prevailing in the solid 18 with which it mixes without altering the volume occupied by the solid 18, whilst the piston 23 slides in the direction of syringe 19. After which the user removes piece 26, the reservoir 21 and the cap-septum 29 (FIG. 14), and the syringe 19 is ready for use for the injection of the preparation which it contains.

Figure 16:
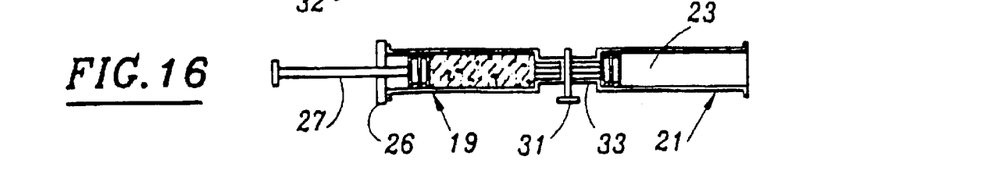
Figure 17:
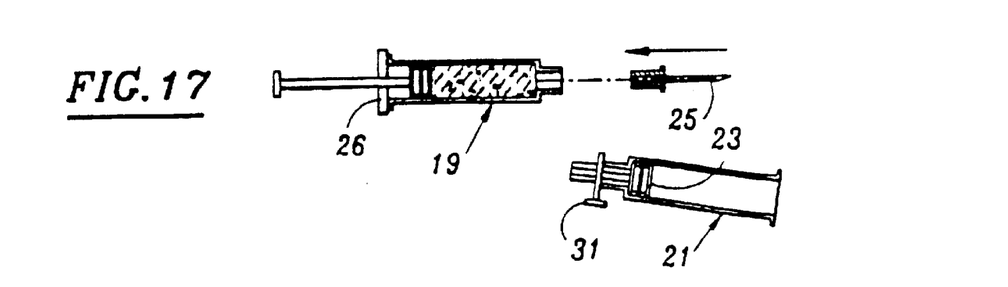
Figure 18:
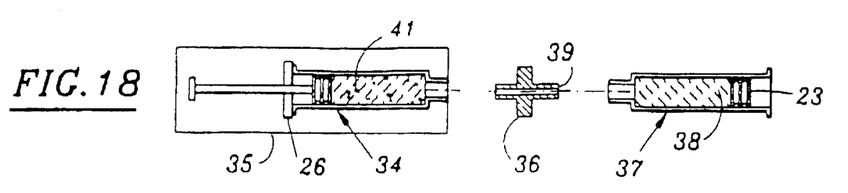
FIGS. 18 to 21 illustrate the implementation of a third embodiment of the process and device according to the invention.
Figure 19:
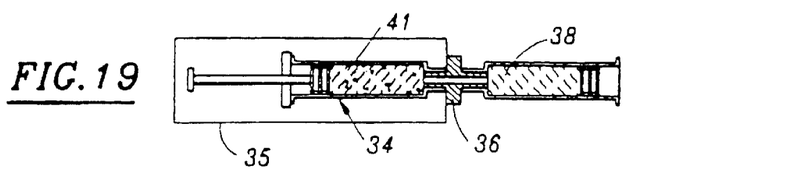
Figures 20, 21:
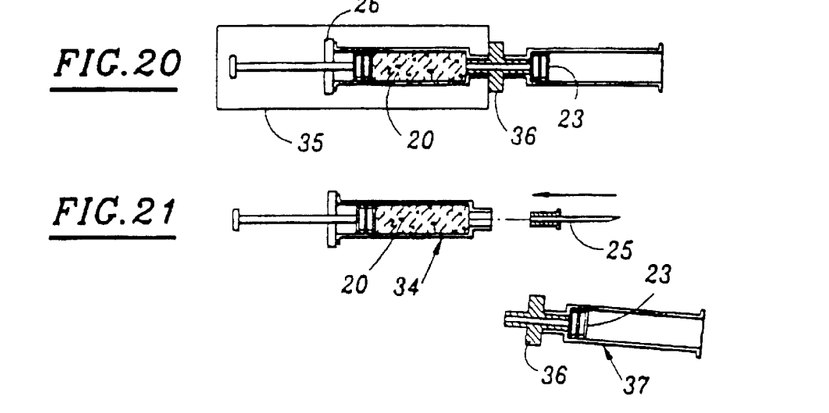

In the example illustrated in FIGS. 15 to 17, the freeze-dried product or solid 18 pre-loaded under vacuum into syringe 19 is connected to the liquid reservoir 21 (here a cartridge as in the example of FIGS. 11 to 14) by way of a valve 31, for example, of the quarter-turn type. Syringe 19 is vacuum-packed in a flexible packaging 32 and fixed to a connector 33 in communication with the liquid reservoir 21, the connector 33 being fitted with valve 31.

Extemporaneous rehydration preparation then consists in opening valve 31 so that the liquid 22 passes automatically, by suction, from cartridge 21 to syringe 19 (FIG. 16) whilst the piston 23 of cartridge 21 travels towards syringe 19. Cartridge 21 and tap 31 (FIG. 17) of syringe 19 are then disconnected in order to fix injection needle 25 to said syringe, the mixture obtained in syringe 19 then being ready to be injected.

In the embodiment of FIGS. 18 to 21, the syringe 34 is vacuum packed in a flexible packaging 35 and fixed to a connector 36 in communication with liquid reservoir 37 composed of a cartridge. The connector 36 serves to pierce the plastic packaging 35 (FIG. 19) and to fix syringe 34 to the reservoir of liquid (water) 37.

The connector 36 is pierced with an axial channel 39 such that the piercing of the plastic packaging 35 by the connector 36 brings into communication the volume of liquid 38 with the solid dry form 41, which operation draws into the latter, via connector 36, the liquid 38 (FIG. 20), the piston 23 accompanying the displacement of the liquid 38. The reservoir 37 thus empties automatically to rehydrate the solid 41. It is then disconnected from syringe 34 (FIG. 21) and the injection needle 25 is fitted to syringe 34.

Figure 22:
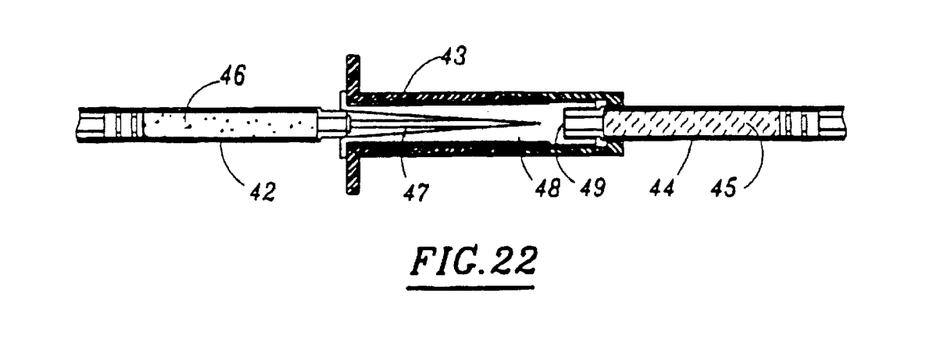
FIG. 22 is a longitudinal elevation of a fourth embodiment of the device according to the invention.

In the embodiment of FIG. 22, the device comprises a syringe 42 connected by a cap 43 to a cartridge-septum 44 containing the liquid 45. The syringe 42 containing the solid (dry form 46) is fitted with an injection needle 47 introduced and kept in place inside the cap 43 in a packing 48 made of a flexible material such as an elastomer, which keeps needle 47 in place inside the cap 43, opposite the septum 49. The needle 47 is then ready to be inserted in the septum 49 to bring about the passage of liquid 45 into the syringe 42 and thus the rehydration of the solid of active principle 46.

Figures 23, 24:
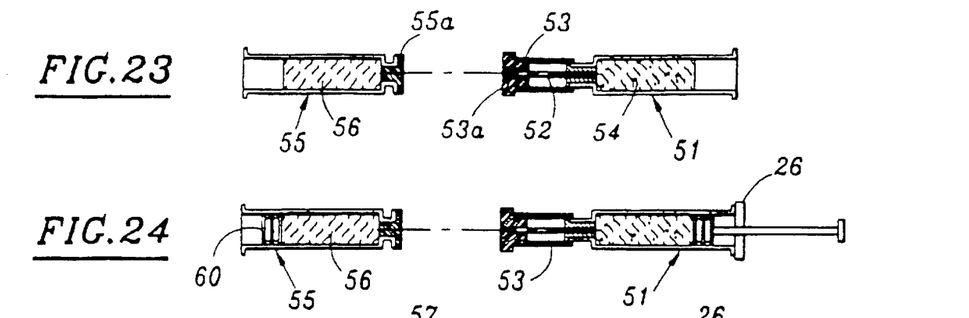
FIGS. 23 to 25 show the successive stages of the preparation and vacuum packing of a fifth embodiment of the device according to the invention.
Figure 25:
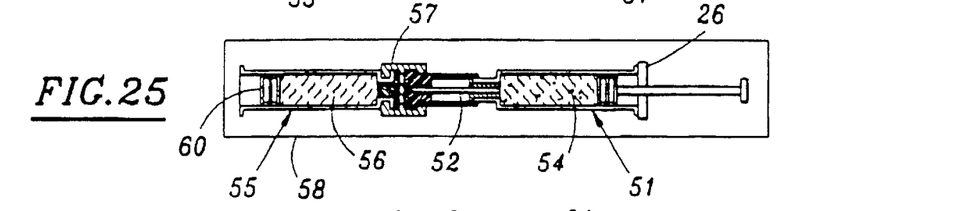

In the embodiment of the device illustrated in FIGS. 23 to 25, the syringe 51 is provided with an injection needle 52 engaged in a cap 53 inside of which it is able to slide in order to bring into communication the interior volume of syringe 51 containing the solid 54 with the reservoir or cartridge 55 containing the liquid 56. These two elements are prepared independently and then combined in an extemporaneous rehydration device (FIGS. 24 and 25) by fixing the cap 53 with the end 55a of cartridge 55 by means of a suitable connection 57 (FIG. 25).

The whole unit is vacuum-packed in a flexible packaging 58, ready for use after removal of this packaging 58, insertion of the needle 52 in the end 55a and suction of the liquid 56 into the solid 54.

The needle 52 is inserted in septum 53a which it pierces completely at the moment of rehydration under vacuum of solid 54 by liquid 56.

In the device illustrated in FIGS. 26 to 29, the process to which the invention relates provides for the addition to the dry form 58 of a layer of excipient 59 which is used subsequent to the injectable preparation as a liquid piston to push the other layers and reduce the losses of active principle during injection.

Figure 26:
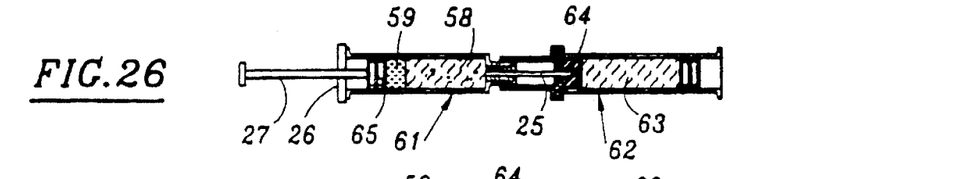
FIGS. 26 to 29 are longitudinal elevations and partial sections illustrating the implementation of a sixth embodiment of the device according to the invention.
Figure 27:
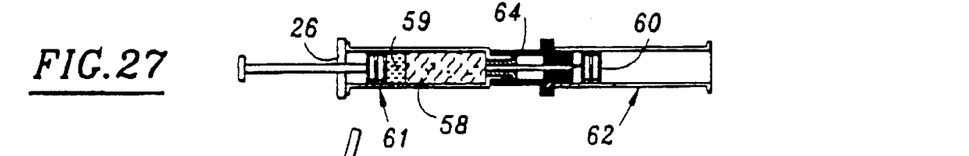
Figure 28:
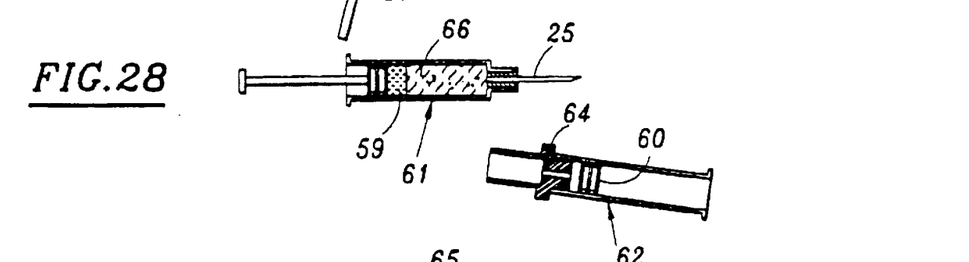

The device comprises, apart from syringe 61 containing the solid active principle 58, a reservoir 62 containing a piston 60 and the rehydration liquid 63 and a cap-septum 64 blocking off the reservoir 62 on the side of syringe 61 and in which is engaged the injection needle 25. The syringe 61 is fitted with piece 26 for retaining its piston 65 and its spindle 27, the piece 26 resting against the end of the body of the syringe.

According to the process, after freezing of the liquid containing the active principle and prior to freeze-drying or drying, a specific quantity of solution of excipient such as mannitol is added to the surface of the frozen liquid. This volume is in turn frozen and the whole unit (58, 59) is then freeze-dried. A volume 59 of freeze-dried product containing only the excipient (mannitol) is thus obtained between piston 65 and the solid 58 of active principle under vacuum. This volume 59, after automatic and static rehydration by piercing of the septum 64 by the needle 25 (FIG. 27) and separation of the reservoir 62, will be used to push the liquid form 66 of active principle. At the end of injection, the volume 59 occupies the dead volumes 59a (FIG. 29) at the bottom of the syringe 61 and of needle 25.

Figure 29:
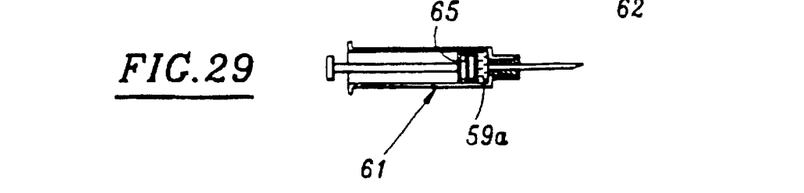

Thanks to liquid piston 59, practically any loss of active principle is avoided, this being an important advantage because of the cost of the active principle.

Figure 30:
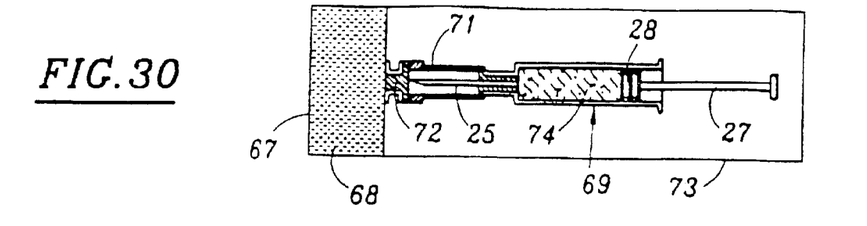
FIGS. 30 to 32 are longitudinal elevations illustrating the implementation of a seventh embodiment of the device according to the invention.
Figure 31:
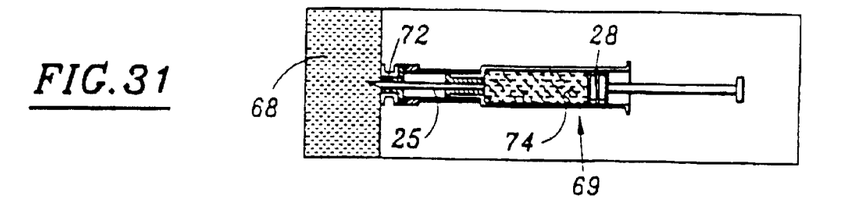

The embodiment of the device illustrated in FIGS. 30, 31 comprises a liquid reservoir composed of a flexible bag 67 containing the volume of rehydration liquid 68. The bag 67 is connected to a syringe 69 by a stopper 71 fitted with a septum 72 ready to be pierced by needle 25. The syringe 69 containing the solid formulation 74 is vacuum-packed in a flexible envelope 73. The needle 25 allows, by pressure on the piston 28, the formulation under vacuum 74 to be connected with its volume of rehydration liquid 68 (FIG. 31).

Figure 32:
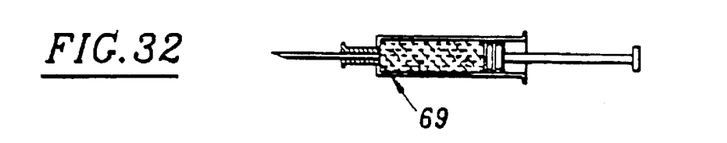
Figure 33:
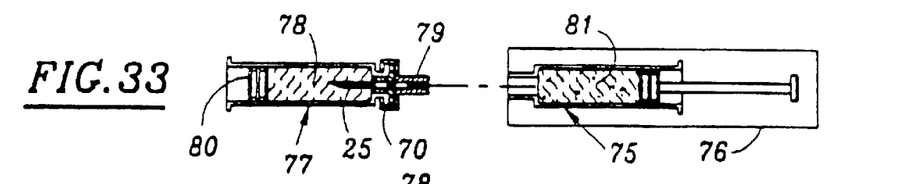
FIGS. 33 to 36 are views illustrating the implementation of an eighth embodiment of the device according to the invention.

Once mixing has taken place, the packaging envelope 73 is removed, the bag 67 is separated and the stopper-septum 71 removed, the syringe 69 then being ready for use (FIG. 32).

Figure 34:
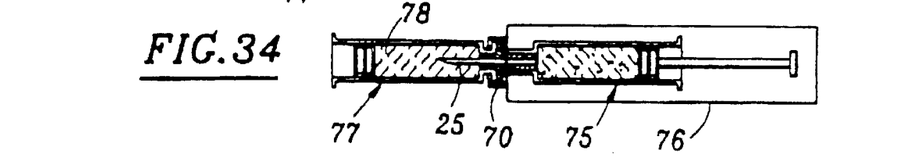

In the embodiment illustrated in FIGS. 33 to 36, the device comprises a syringe 75 packed in a vacuum packaging 76 and a reservoir 77 of liquid 78 fitted with a stopper 70. The injection needle 25 forming a connector by way of its support 79 is introduced beforehand into a cartridge-reservoir 77 through stopper 70. The reservoir 77 may be connected to syringe 75 by piercing packaging 76 by way of the connection 79 (FIG. 34).

Figure 35:
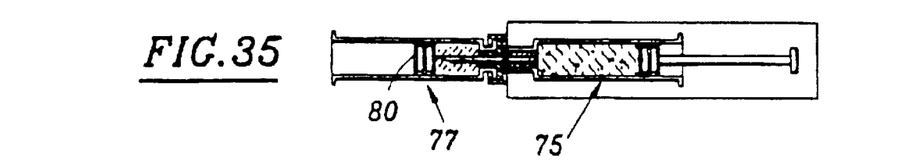
Figure 36:
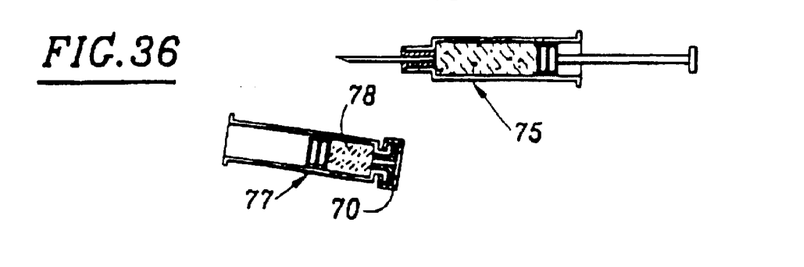

Once this operation has been carried out, the volume of liquid 78 and the solid formulation 81 are brought into communication, with the result that the liquid is drawn into syringe 75 (FIG. 35). After which it is sufficient to remove the cartridge 77, its stopper 70, and the plastic packaging 76 in order to render the syringe 75 ready for use (FIG. 36). In this embodiment, the needle 25 and its support 79 form the connector proper, the needle 25 being introduced beforehand into the stopper 70 of cartridge 77.

Figure 37:
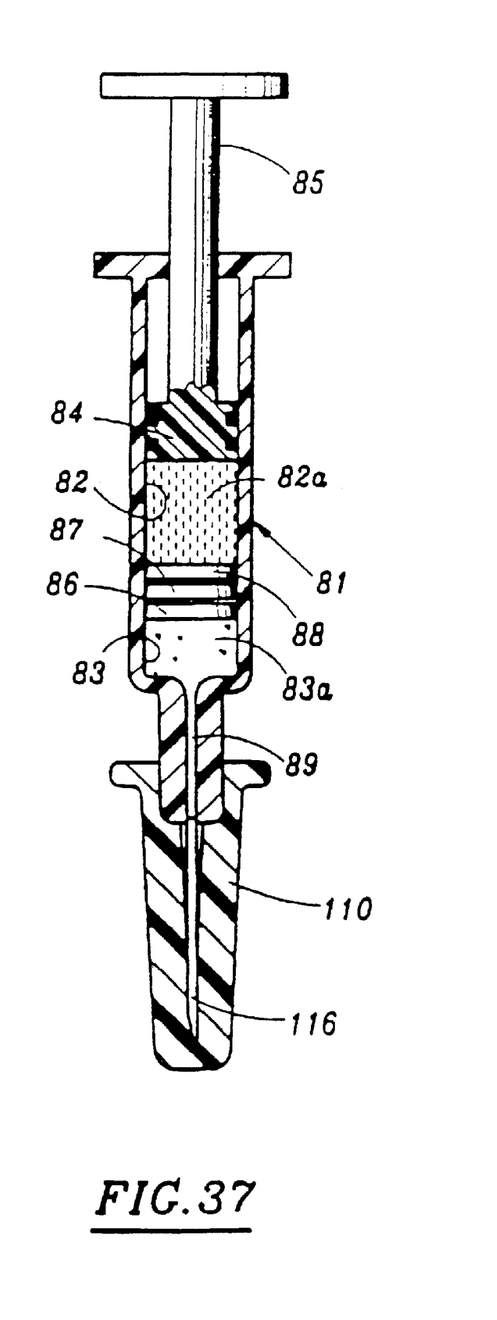
FIGS. 37, 38 and 39 illustrate the successive stages of implementation of a ninth embodiment of the syringe device according to the invention.
Figure 38:
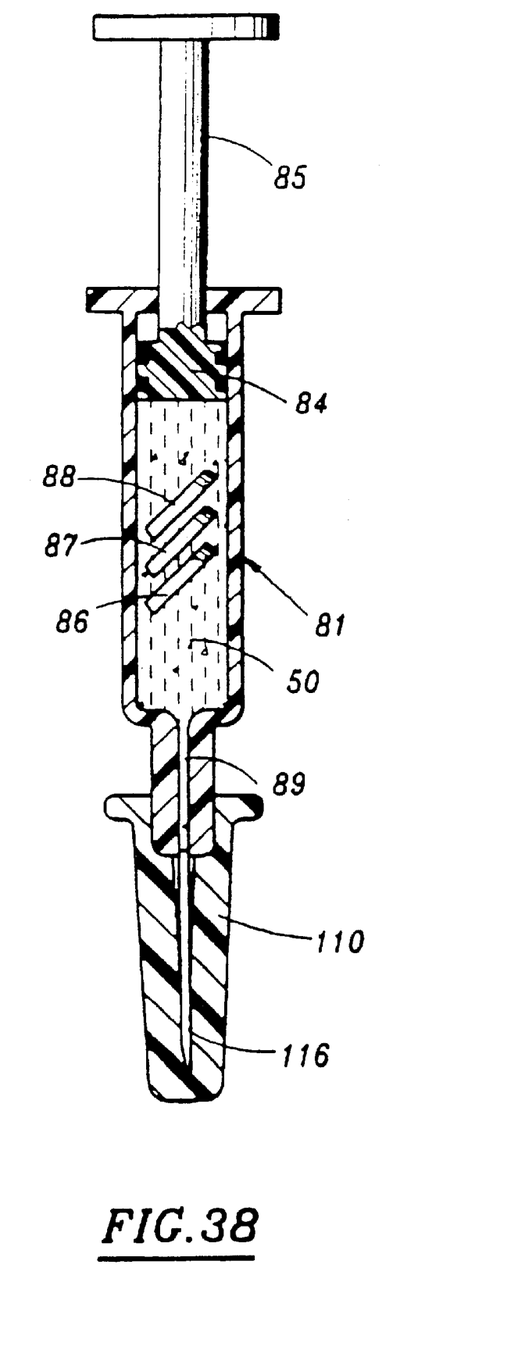
Figure 39:
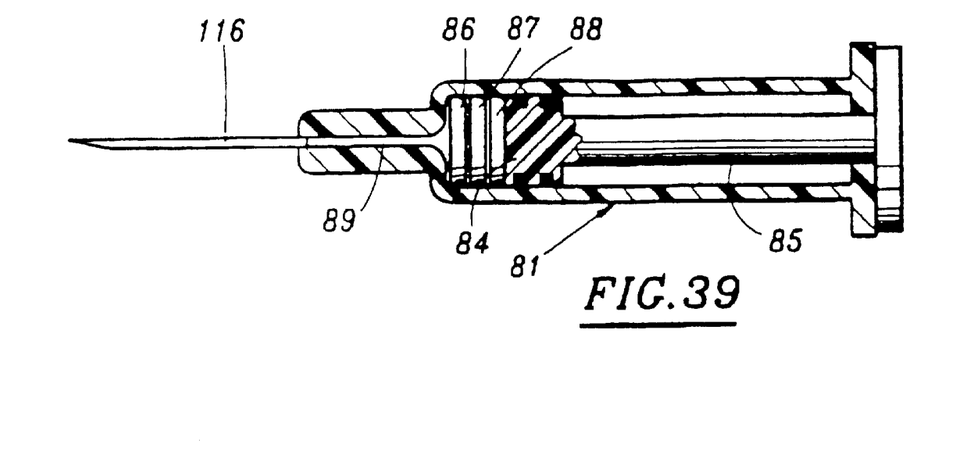

In the embodiment represented in FIGS. 37 to 39, the vacuum packing and rehydration device for the injectable preparation comprises a syringe 81 with a needle 116 enveloped by a stopper 110. This syringe comprises two compartments 82, 83 containing respectively the liquid 82a and the solid formulation 83a. These compartments are delimited by a first piston 84 integral with an activating spindle 85 and by three other independent pistons 86, 87, 88 juxtaposed between the piston 84 and the injection orifice 89. These three pistons 86–88 are independent, that is, not fixed together.

The syringe 81 is loaded with a liquid containing the active principle 83. The preparation is then freeze-dried and the freeze-dried product 83a is vacuum-packed in the bottom of the syringe with the three flat and independent pistons 86, 87, 88. The volume of rehydration liquid 82a is then added to syringe 81 then the piston 84 with its spindle 85, positioned behind the liquid 82a as for a bicompartmental syringe. Piston 84 is made of a standard non-rigid rubber.

Drawing on piston 84 by means of its spindle 85 causes suction of the three flat pistons 86–88 (FIG. 38) which pivot and bring into communication the solid 83a and liquid 82a forms. During this suction and the sliding of piston 84, the solid and liquid forms mix and are mixed by the movement of pistons 86–88. The liquid (for example, water) passes automatically into the solid and reconstitutes the preparation to a liquid of the active principle, which may then be immediately injected (FIG. 39).

This system avoids the specific by-pass syringe and may be implemented by means of a standard syringe.

A flat positioning of the three independent pistons 86–88 in the syringe could prevent good mixing of the liquid/freeze-dried product but the arrangement of the three pistons avoids this risk. The maximum angle of rotation of the pistons is in relation to the distance between the pistons at rest. Said pistons are sufficiently close to one another to avoid a 90° rotation, and as soon as the two chambers 82, 83 communicate, the pistons 86–88 no longer undergo a force likely to displace them to the extent that they come into contact with the injection piston 84.

Figure 41:
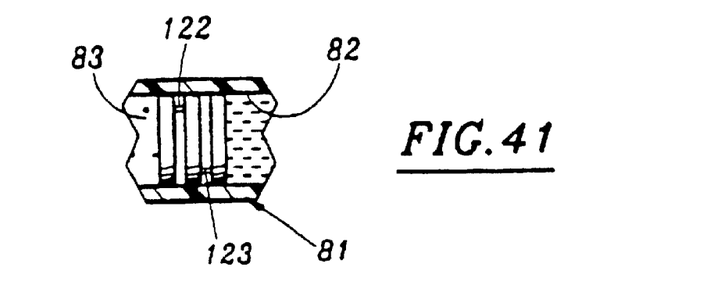
Figure 42:
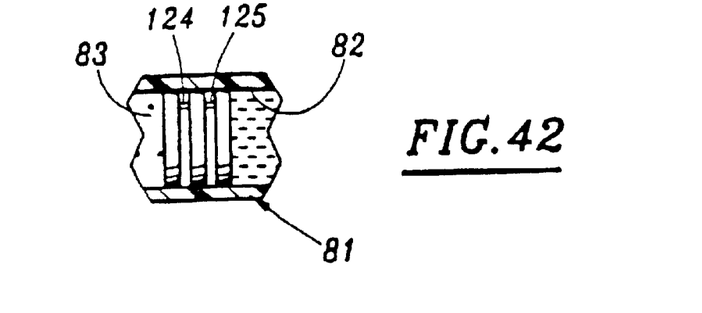

However, for greater security, it is possible, as a variant, to provide between the pistons 86–88 flexible bonds which join them in pairs. These bonds may be centred, such as bonds 120 and 121 (FIG. 40) or asymmetrical: bonds 122, 123 (FIG. 41) or situated on the same side of the axis of the syringe 81: bonds 124, 125 (FIG. 42).

Figure 40:
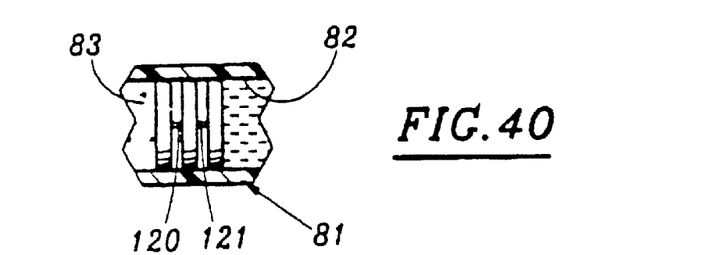
FIGS. 40, 41 and 42 are partial elevations illustrating three possible variants of execution of the embodiment of FIGS. 37 to 39.

Such arrangements make it possible to fix the pistons by a flexible bond, whilst leaving each piston free to pivot.

Figure 43:
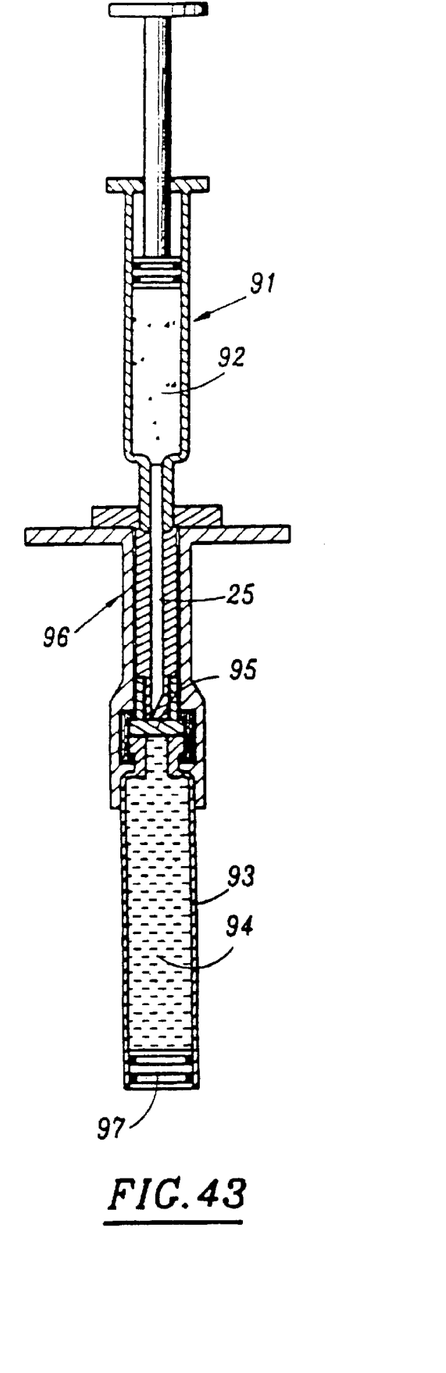
FIG. 43 is a partial section and elevation of a tenth embodiment of the device according to the invention.

The device represented in FIG. 43 comprises a syringe 91 pre-filled with solid under vacuum 92, a cartridge 93 containing the liquid 94 and fitted with a septum 95, and a connector 96 in communication between syringe 91 and the reservoir 93. The injection needle 25 is introduced into connector 96, ready to perforate septum 95.

As soon as the terminal bevel of needle 25 is inserted in septum 95, the solid form 92 and the liquid form 94 are brought into communication and the liquid 94 is sucked into the dry formulation 92 of the syringe 91.

Figure 44:
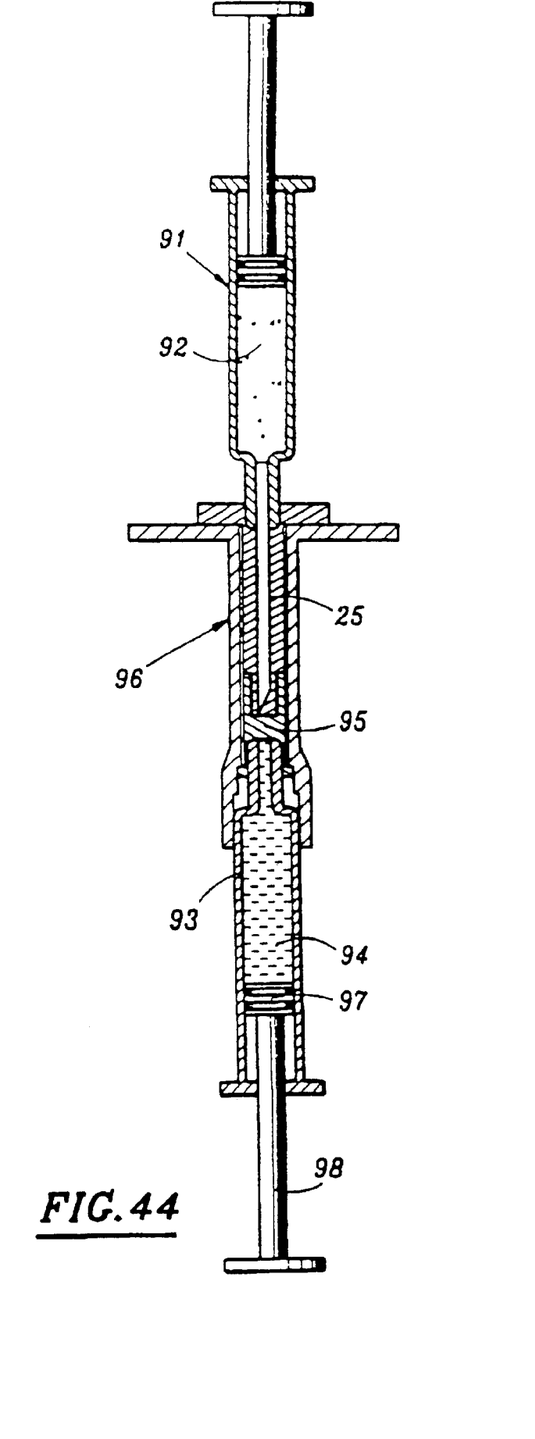
FIG. 44 is a view similar to FIG. 40 of an eleventh embodiment of the device according to the invention.

In the embodiment of FIG. 43 shown in FIG. 44, the piston 97 of the liquid reservoir 93 is fitted with a spindle 98 after the liquid 94 has been introduced into said reservoir 93, this arrangement having the advantage of avoiding any risk of faulty handling.

Figure 45:
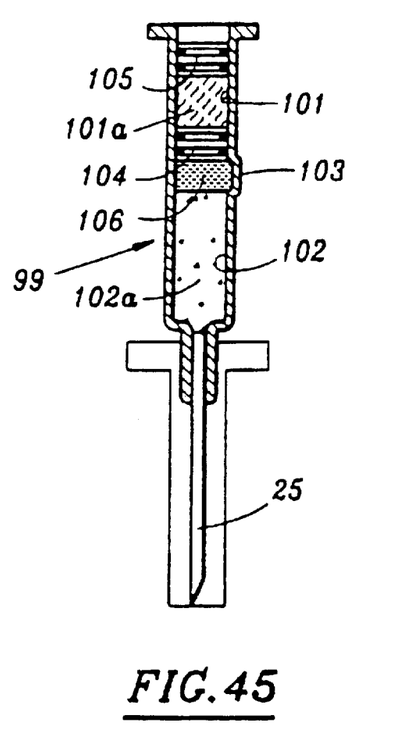
FIG. 45 is a longitudinal section and partial elevation of a twelfth embodiment of the syringe device according to the invention.

In the embodiment of FIG. 45, the device comprises a syringe 99 of the two-compartment type 101, 102 separated by a central by-pass 103 obtained by a local lateral recess of the wall of the syringe leading to an increase in the cross section at that location. One of the two compartments, namely compartment 101 having to contain the rehydration liquid 101a, contains two independent pistons 104, 105 between which the liquid may be placed.

The process for implementing the injectable preparation by means of this device is as follows.

Into the compartment 102 contained between the by-pass 103 and the injection needle 25, a liquid is loaded and frozen, said liquid containing the active principle 102a, and a solution of excipient 106 is added at by-pass 103 and then in turn frozen. The excipient may be a cold dilute solution of mannitol. The whole unit is freeze-dried under vacuum, the first piston 104 is arranged on the excipient under vacuum 106, the second compartment 101 is filled with liquid 101a, the second piston 105 is placed on liquid 101a, the spindle (not shown) of the second piston 105 is installed.

By means of this second piston 105, a pressure is exerted which crushes the excipient freeze-dried under vacuum 106, with the result that the first piston 104 slides and reaches the level of by-pass 103; the liquid 101a then passes automatically via the by-pass 103 into the first compartment 102 and rehydrates the solid under vacuum 102a, and finally the preparation ready to be injected is obtained.

The advantage of the system compared with the conventional use of by-passes is to avoid non-loaded re-solution or re-suspension volumes and to make it possible to fill the wasted volumes at the by-pass, the pistons at the bottom of the syringe and of the needle with a liquid preparation without active principle, provided that the rehydrated active principle does not become mixed with the rehydrated excipient before injection. This is the case, for example with microspheres of PLGA (polylactic-glycic acids).

It is thus possible to load, for example, a quantity of 2 ml and more into a by-pass syringe 99 initially intended only for 1 ml.

Figure 46:
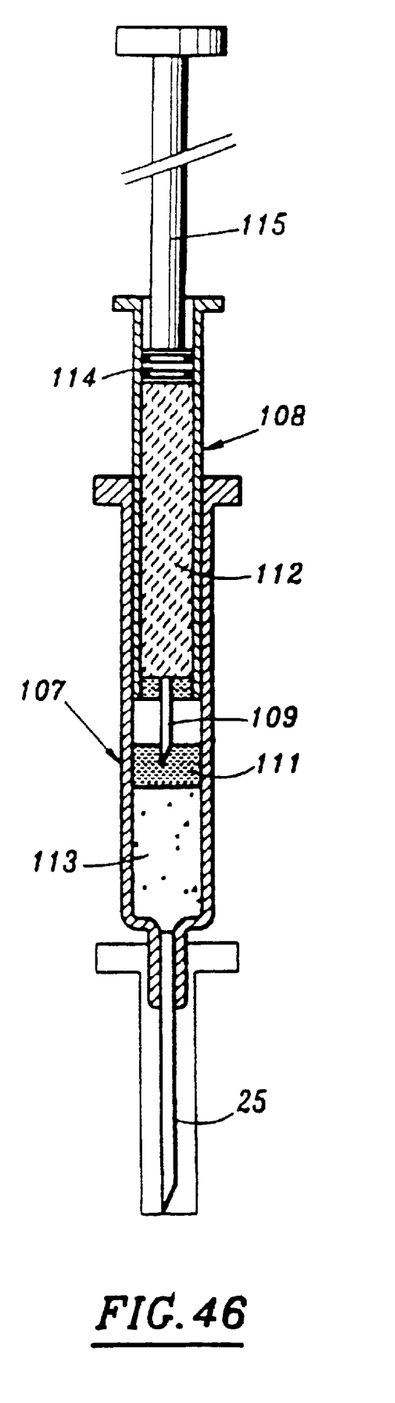
FIG. 46 is a longitudinal section and partial elevation of a thirteenth embodiment of the packing device provided by the invention.

The device illustrated in FIG. 46 comprises a syringe 107 fitted with an injection needle 25 and containing a cartridge-septum 108. This latter is fitted with a short needle 109 blocked off by insertion in an injection piston 111 of syringe 107. The cartridge-septum 108 may contain the rehydration liquid 112 and the syringe 107 may contain the dry form 113.

The cartridge-septum 108 is fitted with a piston 114 and a spindle 115 of sufficient length to be able to use the cartridge-septum 108 as a spindle of the injection piston 111. The cartridge-septum 108, which is the equivalent of a small syringe with its short needle 109, is pre-filled with liquid 112 and positioned in the barrel of the syringe 107. The short needle 109 is blocked off by insertion in the injection piston 111. Activation of the device is obtained by inserting the needle 109 of the cartridge-septum 108 in the injection piston 111. This insertion makes it possible to pass the liquid 112 into the reservoir of the syringe 107 contained between the injection piston 111 and needle 25 and which contains the solid under vacuum 113, which operation ends in the reconstitution of the injectable preparation.

In this type of embodiment, the injection piston 111 acts as a septum or barrier between the volume of liquid 112 and the solid under vacuum 113. Thus, the device as a whole is in the same syringe 107, and the needle 25 is not used to pierce the septum and to serve as a connecting element.

In order-to obtain the dry form, in the case of a semi-solid, the liquid dispersion is loaded into the syringe 107, freeze-dried or dried and vacuum-packed with the injection piston 111.

The product obtained by implementing the device and the process which have just been described in the various embodiments illustrated in the drawings comprises, in a general manner, a dry form for parental administration and vacuum-packed inside an injection device also containing a liquid volume, ready to be mixed by suction with the dry form in order to reconstitute the injectable preparation.

The dry form may be a freeze-dried form or a powder obtained after removal of a solvent.

The dry form may contain the active principle alone, or the active principle and an injectable excipient, for example, mannitol.

The volume containing the dry form under vacuum is equal to the volume occupied by the injectable preparation obtained after mixing the dry form with the necessary liquid.

The liquid may be water, or an aqueous medium, or an organic solvent with or without water, or an anhydrous liquid or injectable oil.

The injectable preparation obtained may be a liquid solution, or a solid suspension in a liquid, or a gel or a semi-solid dispersion.

The vacuum required for the process of preparation according to the invention is a vacuum sufficient to draw a stream of reconditioning liquid prior to injection (hydration or other) into the whole of the volume to be injected without leaving air bubbles, dead spaces or a zone of product that is still dry.

According to conventional processes for packing dry or freeze-dried injectable products, it is possible to use a "partial vacuum" of air or inert gas (nitrogen) before closing the reservoir containing the dry form in order to avoid excess pressure after stoppering.

This partial vacuum may be offset by stoppering with a return to atmospheric pressure, or a pressure slightly below atmospheric may be maintained in the bottle or in the syringe in order to prevent excess pressure during the addition of the liquid medium.

It is possible, of course, to stopper a bottle under a "total vacuum" after freeze-drying, but this does not have any advantage for reconditioning the solid apart from the precise case of the invention where the solid occupies the entire volume under vacuum, and where the liquid comes to occupy exactly this volume under vacuum directly in the injection device (syringe).

The partial vacuum may be between 0.9 and 0.6 atmospheres. The total vacuum may be defined as the vacuum corresponding to less than ½ atmosphere and advantageously to low pressures of $1/10$ atmosphere and less.

This total vacuum may also be defined as the vacuum obtained by a vacuum pump used, for example, for a freeze-dryer. A rotary pump with a two-stage valve may reach $1.10^{-3}$ mbar or 1 $\mu$bar.

The vacuum used for the invention may thus be less than 100 mbar or advantageously less than 10 mbar or even less than 0.1 mbar.

What is claimed is:

1. A process for preparing a liquid injectable preparation, comprising the steps of:

providing an injection device from which the preparation can be ejected; said injection device having a reservoir defining an internal volume;

said reservoir being an injection chamber of a syringe for injecting the liquid injectable preparation via an injection needle;

providing a dry form of an active principle under vacuum in the internal volume of the reservoir;

providing a liquid in which said dry form can be dissolved or suspended to form said liquid injectable preparation; and extemporaneously introducing said liquid into said dry form by suction by virtue of the action of the vacuum in order to form said liquid injectable preparation in said reservoir, from which said preparation can be injected.

2. The process according to claim 1, wherein the total vacuum is a vacuum lower than 100 mbars.

3. The process according to claim 1, wherein the total vacuum is a vacuum lower than 10 mbars.

4. The process according to claim 1, wherein the total vacuum is a vacuum lower than 0.1 mbar.

5. The process according to claim 1, further comprising adding a layer of excipient to the dry form, and using said layer subsequent to the injection preparation as a liquid piston to push other layers and to reduce losses of active principle during injection.

6. The process according to claim 5, further comprising packing the dry form in the syringe fixed to an automatic rehydration device, and in order to prepare the dry form, freezing a liquid containing the active principle, adding a specific quantity of excipient solution to the surface of the frozen liquid to obtain a unit including frozen excipient solution, freeze-drying the unit thereby to obtain, between a piston of the syringe and the solid of active principle under vacuum, a volume of freeze-dried product containing only the excipient, which after automatic rehydration and movement of the piston in order to empty the syringe, occupies after injection a dead volume at the bottom of the syringe and of the injection needle.

7. The process according to claim 1, wherein the dry form is prepared in the syringe which comprises a bypass of increased cross-section in a median zone of the syringe, the process further comprising loading and freezing a first liquid containing the active principle in a first compartment disposed between the bypass and an injection needle, adding a solution of excipient at the bypass to obtain a unit including frozen solution, freeze-drying the unit under vacuum, arranging a first piston on the excipient under vacuum, filling a second compartment with a second liquid, placing a second piston on the second liquid, installing a spindle of the second piston, exerting a pressure by the second piston which crushes the freeze-dried excipient with the result that, when the first piston reaches the bypass, the second liquid automatically passes via the bypass into the first compartment and rehydrates the solid under vacuum to obtain the liquid injectable preparation.

8. A device for implementing the process according to claim 1, which comprises a reservoir disposed in an injection device for vacuum packing a dry form, said injection device being a vacuum-packed gas tight syringe, means of packing a liquid for extemporaneous rehydration comprising a reservoir containing a piston, and connection means between the reservoir and the means for packing in order to add, by suction, the liquid to the dry form.

9. The device according to claim 8, wherein the dry form occupies the entire volume of the reservoir after said extemporaneous rehydration.

10. The device according to claim 8, wherein the connection means comprise either a septum and an injection needle, or a tap.

11. The device according to claim 8, wherein the syringe is vacuum-packed in a flexible packaging and fixed to a connector in communication with the liquid reservoir.

12. The device according to claim 8, wherein the syringe is provided with an injection needle engaged in a cap and adapted to slide therein in order to bring the syringe into communication with the liquid reservoir, and the entire unit being packed in a vacuum packaging.

13. The device according to claim 8, wherein the liquid reservoir is a flexible bag linked by a stopper-septum to the vacuum-packed syringe.

14. The device according to claim 8, wherein the syringe is packed in a vacuum packaging and provided with an injection needle forming a connector, introduced into the liquid reservoir through a stopper and joined to the syringe through the packaging.

15. The device according to claim 8, wherein the syringe comprises two compartments delimited by a first piston integral with an active spindle and by independent pistons, optionally linked together.

16. The device according to claim 8, wherein the syringe comprises two compartments separated by a central bypass and one of the two compartments, designed to contain the rehydration liquid, includes two independent pistons having a space therebetween for the liquid.

17. The device according to claim 8, wherein the syringe contains a cartridge septum provided with a needle blocked off by insertion in an injection piston of the syringe, the cartridge septum adapted to contain the rehydration liquid and the syringe adapted to contain the dry form.

18. The device according to claim 17, wherein the cartridge-septum is fitted with a piston and a spindle of sufficient length to enable use of the cartridge-septum as a spindle of the injection piston, after insertion of the needle of the cartridge-septum in the injection piston in order to pass the liquid contained in the cartridge-septum into the reservoir of the syringe disposed between the injection piston and the injection needle, and containing a solid under vacuum, thereby making it possible to reconstitute the injectable preparation.

19. The device according to claim 8, wherein the syringe is joined by a cap to a cartridge-septum containing the liquid, the syringe being fitted with an injection needle introduced and kept in place inside the cap, opposite the septum of the cartridge-septum, ready to be inserted in the septum in order to bring about rehydration of the solid of active principle contained in the syringe.

20. A product obtained by implementing the process according to claim 1, comprising a dry form for parenteral administration and vacuum-packed inside a syringe for injecting the liquid injectable preparation and injection needle also containing a liquid volume ready to be mixed by suction with the dry form in order to reconstitute the injectable preparation.

21. The product according to claim 20, wherein the dry form occupies the entire volume of the vacuum-packed reservoir.

22. The product according to claim 20, wherein the dry form is a freeze-dried form or a powder obtained after removal of a solvent.

23. The product according to claim 20, wherein the dry form contains the active principle and mannitol as a injectable excipient.

24. The product according to claim 20, wherein the volume containing the dry form under vacuum is equal to the volume occupied by the injectable preparation obtained after mixing the dry form with the necessary quantity of liquid.

25. The product according to claim 20, wherein the liquid is selected from the group consisting of water, an aqueous medium, an organic solvent with or without water, an anhydrous liquid, and an injectable oil.

26. The product according to claim 20, wherein the injectable preparation is selected from the group consisting of a liquid solution, a solid suspension in a liquid, a gel, and a semi-solid dispersion.

* * * * *